United States Patent [19]

Detty et al.

[11] 4,431,586

[45] Feb. 14, 1984

[54] MONOCYCLIC TELLUROPYRONES

[75] Inventors: Michael R. Detty; Bruce J. Murray; Jerome H. Perlstein, all of Rochester, N.Y.

[73] Assignee: Eastman Kodak Company, Rochester, N.Y.

[21] Appl. No.: 279,361

[22] Filed: Jul. 1, 1981

[51] Int. Cl.³ .............................................. C07D 345/00
[52] U.S. Cl. ................................................ 260/239 R
[58] Field of Search ................................... 260/239 R

[56] References Cited

PUBLICATIONS

N. Dereu & M. Renson, Ph. D. Thesis, University, Liege, Belgium, Journal of Organometallic Chemistry, vol. 208, pp. 11–21, 1981.

N. Dereu & M. Renson, Phosphorous and Sulfur, vol. 6, p. 73, 1979.

W. Lohner & K. Praefcke, Chem.-Ztg., vol. 103, p. 265, 1979.

W. Lohner, J. Martens, K. Praefcke, & H. Simon, Journal of Organometallic Chemistry, vol. 154, pp. 263–271, 1978.

Primary Examiner—Paul M. Coughlan, Jr.
Assistant Examiner—D. B. Springer
Attorney, Agent, or Firm—John R. Everett

[57] ABSTRACT

The present invention discloses novel mononuclear telluropyrone compositions of matter and a method for making such compositions. The compositions are useful intermediates for making telluropyrylium electron accepting dye sensitizers for photoconductive compositions.

4 Claims, No Drawings

MONOCYCLIC TELLUROPYRONES

FIELD OF THE INVENTION

This invention relates to novel mononuclear telluropyrone compositions of matter, a method for making such compositions, and their utility as intermediates in the preparation of telluropyrylium electron accepting dye sensitizers for electron donating photoconductive composition and elements.

Chalcogen-containing organic compositions of matter are known. Some benzofused telluropyrones, such as tellurochromones and telluroxanthones, have been prepared. Also a method for preparing tellurophenes is known. However, none of the foregoing methods are useful in making mononuclear telluropyrones.

SUMMARY OF THE INVENTION

The present invention provides novel compositions of matter having a mononuclear telluropyrone nucleus. (Referred to sometimes hereinafter as telluropyrones or telluropyrone compositions of matter). This invention also provides a method for making mononuclear telluropyrone. In the context of the present invention, "mononuclear" means that no fused aromatic rings are attached to the telluropyrone nucleus. Also the term "telluropyrones" include telluropyrone thiones.

The compositions of matter of the invention are useful as intermediates in the preparation of telluropyrylium telluroyrylium boron diketonates and phosphorous diketonate sensitizers for photoconductive composition. Such sensitizers are disclosed in commonly assigned U.S. patent application Ser. No. 279,365, now U.S. Pat. No. 4,365,017 granted Dec. 21, 1982, entitled "Telluropyrylium Electron Accepting Dye Sensitizers For Electron Donating Photoconductive Compositions" and U.S. patent application Ser. No. 279,363, now U.S. Pat. No. 4,365,016 granted Dec. 21, 1982, entitled "Benzotelluropyrylium Diketonate Electron Accepting Dye Sensitizers For Electron Donating Photoconductive Compositions," both in the name of Detty et al, and filed on the same date as the present case.

The novel method of our invention comprises the steps of:

contacting an alkyl alcohol solution containing a telluride dianion and an alkoxide anion with a solution containing a pentadiynone, thereby forming compositions of matter having a mononuclear telluropyrone nucleus. For the purpose of this invention described herein, the term "pentadiynone" includes the sulfur and selenium counterparts of pentadiynone.

The thus formed mononuclear telluropyrone compositions are, if desired, isolated by any separation technique for isolating and purifying chemical compounds. Many such techniques are well known and will be referred to more specifically hereinafter.

PREFERRED EMBODIMENTS

In a preferred embodiment, the mononuclear telluropyrone compositions of the present invention are prepared by:

contacting, generally admixing, an alkyl alcohol solution containing a telluride dianion and an alkoxide anion with a solution containing a pentadiynone wherein the pentadiynone has the structure:

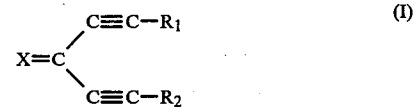

and the resulting composition of matter has a mononuclear telluropyrone nucleus having the structure:

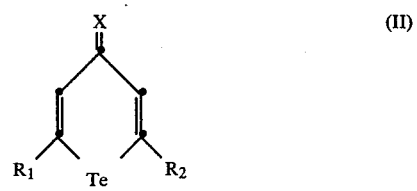

wherein $R_1$ and $R_2$ each independently represents aryl, a monocyclic or polycyclic heteroaromatic group, alkyl, alkoxy, amino, trialkylsilyl, triarylsilyl, alkylamino, dialkylamino or halogen; and X represents O, S or Se.

"Aryl," which is substituted or unsubstituted, refers to substituents such as phenyl, naphthyl, anthryl, methoxy phenyl, alkoxy phenyl, dialkylamino phenyl, alkyl phenyl, nitrophenyl and halophenyl. "Alkyl" and alkoxy refer to a branched- or straight-chain hydrocarbon having up to 16 carbon atoms, such as methyl, ethyl, propyl, isopropyl, butyl, dodecyl, nonyl or isobutyl. "Mono- and polycyclic heteroaromatic groups" refer to aromatic groups having hetero atoms such as O, N, S, Se or Te. Examples of the latter groups include the groups generally used to form cyanine dyes, such as pyridyl, furaryl, thiophenyl, selenopenyl, tellurophenyl, oxazolyl, thiazolyl, selenazolyl, tellurazolyl, benzoxazolyl, benzthiazolyl, benzselenazolyl or benztellurazolyl.

Substituents on alkyl, aryl and heteroaromatic groups include alkyl, aryl, halogen, nitro, cyano, carboxy, hydroxy, alkoxy, amido, aryl, amino, alkylamino, dialkylamino, trialkylsilyl, alkylarylsilyl, triarylsilyl, alkylthio, arylthio, or aryloxy.

DETAILED PRESENTATION OF THE INVENTION

The method of the present invention is useful in making a wide variety of mononuclear telluropyrones.

Alkyl alcohols which are useful in the method of the present invention include ethanol, propanol, isopropanol, methanol, n-butanol, isobutanol, or tert-butanol. All of these alcohols are readily available from a variety of chemical manufacturing companies. Also, methods for making alkyl alcohols are well known in the chemical literature.

Suitable starting materials for the alkoxide anion include alkali and alkaline earth alkoxides such as sodium methoxide, sodium ethoxide, sodium isopropoxide, potassium tert-butoxide, potassium ethoxide, potassium methoxide, potassium isopropoxide, sodium butoxide or potassium butoxide. Alkoxides are, as in the case of alkyl alcohols, readily available in the chemical industry. Methods for the preparation of useful alkoxide anions are also well known in the chemical literature.

Useful pentadiynones, including pentadiynethiones, include 1,4-pentadiyn-3-one, 2,5-heptadiyn-4-one, 1,5-diphenyl-1,4-pentadiyn-3-one, 1,5-di(p-dimethylaminophenyl)-1,4-pentadiyn-3-one, 1,7-bis-(trimethylsilyl)-2,5-heptadiyn-4-one, 1,5-bis(trimethylsilyl)-1,4-pentadiyn-3-one, 1,5-diphenyl-1,4-pentadiyn-3-thione or 1-phenyl-1,4-hexadiyn-3-one. Pentadiynones are readily prepared according to the methods disclosed by Chauvelier in *Ann. Chim.*, (Paris), 1948, 12, 410, and by Normant and Bourgain in *Tetrahedron Lett.*, 1970, 2659.

The telluride dianion used in the method of this invention is conveniently prepared by reacting elemental tellurium with a reducing agent, such as lithium triethylborohydride. Other suitable reducing agents include diisobutylaluminum hydride, sodium in liquid ammonia, lithium in liquid ammonia, potassium borohydride or sodium borohydride. In this reaction, the tellurium is added to 2.0 to 3.0 equivalents of a 0.2 to 1.0 molar solution of the reducing agent in a solvent such as tetrahydrofuran. Other useful solvents include ether for lithium triethylborohydride, ammonia for alkali metals, ethanol for hydrides or water for hydrides. The mixture is stirred at ambient temperature under an inert atmosphere, such as nitrogen, for 1 to 15 hours. Other sources of telluride dianions are obtained by treating bis(trialkylsilyl)tellurides with a fluoride source such as tetra-n-butylammonium fluoride in a solvent such as acetonitrile or tetrahydrofuran.

In general, the method of this invention is carried out simply by admixing from about 0.2 to 2.0 moles of telluride dianion, about 0.02 to 2.0 moles of the alkoxide anion and about 0.2 to 2.0 moles of the pentadiynone in a solution of an alkyl alcohol in another solvent such as tetrahydrofuran. The mixing is carried out at about 0° C. The order of addition of the reagents to the alkyl alcohol-tetrahydrofuran solution is unimportant. However, best results are obtained when the tellurium dianion is first added to a solution of the alkoxide anion in the appropriate alkyl alcohol and the resulting mixture is added dropwise to an alkyl alcohol-tetrahydrofuran solution containing the pentadiynone.

Solvents which are useful other than tetrahydrofuran are ether, glyme or diglyme.

Telluropyrones can be converted to telluropyrone thiones by any of the known procedures used to convert ketones to thiones. Useful procedures are described by Pederson, Scheibye, Nilsson, and Lawesson in *Bull. Soc. Chim. Belg.*, 1978, 87, 223. One useful method involves refluxing a toluene solution of the telluropyrone in toluene with a sulfurating material obtained from phosphorous pentasulfide and anisole. This procedure is carried out in Example 2 and Example 4 herein.

Telluropyrones, including telluropyrone thiones, are converted to pyrylium type dyes by using any of the well-known methods for converting pyrones to pyrylium dyes.

The novel telluropyrones are isolated from the reaction mixture and purified using conventional chemical separation methods and techniques for isolation and purification of chemical compounds. Such methods and techniques include soaking the crude reaction mixture with cold water, removing the product by extraction with a water-imiscible solvent such as a halogenated solvent, drying, precipitation by concentration, and recrystallization from an organic solvent such as methanol when the products are solids, or separating chromatographically when the products are liquids.

A partial listing of the telluropyrones which are made according to this invention are as follows:
1. 2,6-dimethyltelluropyrone
2. 2,6-dimethyltelluropyrone thione
3. 2,6-diphenyltelluropyrone
4. 2,6-diphenyltelluropyrone thione
5. 2-phenyl-6-methyltelluropyrone
6. 2,6-di(4-pyridyl)telluropyrone
7. 2,6-diethyltelluropyrone
8. 2,6-di(p-methoxyphenyl)telluropyrone
9. 2,6-di(trimethylsilylmethyl)telluropyrone
10. 2,6-di(N,N-dimethylanilino)telluropyrone The following examples illustrate the method of this invention:

EXAMPLE 1

Preparation of 2,6-Diphenyltelluropyrone

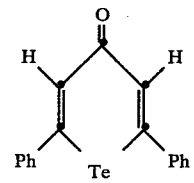

Tellurium (2.55 g) was added to 40 milliliters of a 1 molar solution of lithium triethylborohydride in tetrahydrofuran under a nitrogen atmosphere. The resulting mixture was stirred at ambient temperature for 15 hours. A 1 molar solution of sodium ethoxide in ethanol was prepared by dissolving sodium metal (1.84 g) in 80 milliliters of absolute ethanol. The resulting solution was added to the dilithium telluride giving a deep purple color. After stirring 4 hours, the resulting solution was added dropwise at 0° C. to a solution of 1,5-diphenyl-1,4-pentadiyn-3-one (4.60 g) in 50 milliliters of ethanol and 50 milliliters of tetrahydrofuran. After addition was complete, the reaction mixture was stirred 1 hour at 0° C. and was then concentrated. The residue was partitioned between methylene chloride (500 milliliters) and water (200 milliliters). The aqueous phase was extracted with additional methylene chloride (2×100 milliliters). The combined organic extracts were dried over sodium sulfate and concentrated. Chromatography of the residue on silica gel eluting with 15% ethyl acetate-methylene chloride gave the telluropyrone. Recrystallization from methanol gave 1.51 g (21%) of a yellow, crystalline solid having a melting point of 127.5°–129° C.

EXAMPLE 2

Preparation of 2,6-Diphenyltelluropyrone Thione

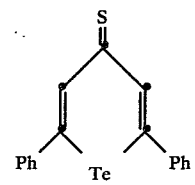

The sulfurating species obtained from phosphorous pentasulfide and anisole (0.22 g, 0.56 mmol) was dissolved in 10 milliliters of hot toluene. 2,6-Diphenyltelluropyrone (0.20 g) was dissolved in 10 milliliters of warm toluene. The two solutions were mixed and the resulting solution was warmed at reflux for 1 minute. The reaction mixture was concentrated. The residue was purified by chromatography on silica gel eluting with methylene chloride. Recrystallization from toluene gave 0.19 g (91%) of a red solid having a melting point of 120°–123° C.

EXAMPLE 3

Preparation of 2,6-Dimethyltelluropyrone

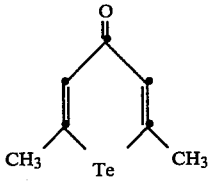

Telllurium (5.10 g) was added to 80 milliliters of a 1 molar solution of lithium triethylborohydride in tetrahydrofuran under a nitrpogen atmosphere. The resulting mixture was then added dropwise at 15° C. to a solution of 2,5-heptadiyn-4-one (4.24 g) in 80 milliliters of tetrahydrofuran and 80 milliliters of 0.01 molar sodium methoxide in methanol. After addition was complete, the reaction mixture was stirred 1 hour at ambient temperature and was then concentrated. The residue was partitioned between methylene chloride (500 milliliters) and water (250 milliliters). The organic extract was dried over magnesium sulfate and concentrated. Chromatography of the residue on silica gel eluting with 5% acetone-methylene chloride gave 1.50 g (16%) of a tan solid. Recrystallization from hexane gave pale yellow needles, mp 95°–97° C.

EXAMPLE 4

Preparation of 2,6-Dimethyltelluropyrone Thione

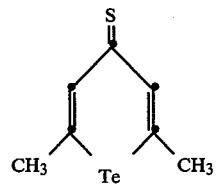

The sulfurating species obtained from phosphorous pentasulfide and anisole (0.50 g) was dissolved in 30 milliliters of boiling toluene. 2,6-Dimethyltelluropyrone (1.0 g) dissolved in 30 milliliters of toluene was added to the solution of the sulfurating agent. The reaction mixture was concentrated. The residue was purified by chromatography on silica gel eluting with methylene chloride to give 0.67 g (65%) of dark brown needles, mp 107°–110° C.

The structure of each compound prepared was confirmed by NMR analysis, infrared spectral analysis, mass spectral analysis and elemental analysis.

The invention has been described in detail with particular reference to preferred embodiments thereof, but it will be understood that variations and modifications can be effected within the spirit and scope of the invention.

We claim:
1. A monocyclic telluropyrone compound .
2. A monocyclic telluropyrone compound having the structure:

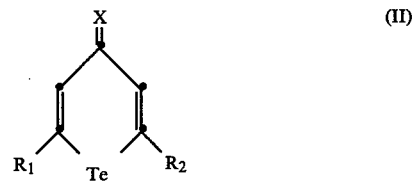

(II)

$R_1$ and $R_2$ each independently represents aryl, alkyl, hydrogen, alkoxy, amino, trialkylsilyl, triarylsilyl, alkylamino, dialkylamino or halogen;
X represents O, S or Se.
3. A compound as in claim 2 wherein $R_1$ and $R_2$ represent methyl or phenyl; and X represents O or S.
4. A compound selected from the group consisting of 2,6-diphenyltelluropyrone; 2,6-diphenyltelluropyrone thione; 2,6-dimethyltelluropyrone; 2,6-dimethyltelluropyrone thione or 2-phenyl-6-methyltelluropyrone.

* * * * *